(12) United States Patent
Kang et al.

(10) Patent No.: US 9,782,175 B2
(45) Date of Patent: Oct. 10, 2017

(54) SYSTEMS, METHODS AND APPARATUSES FOR REAL-TIME ANASTOMOSIS GUIDANCE AND SURGICAL EVALUATION USING OPTICAL COHERENCE TOMOGRAPHY

(71) Applicant: The Johns Hopkins University, Baltimore, MD (US)

(72) Inventors: Jin U. Kang, Ellicott City, MD (US); Yong Huang, Baltimore, MD (US); Gerald Brandacher, Baltimore, MD (US); Zuhaib Ibrahim, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 142 days.

(21) Appl. No.: 14/261,275

(22) Filed: Apr. 24, 2014

(65) Prior Publication Data

US 2015/0305822 A1    Oct. 29, 2015

(51) Int. Cl.
*A61B 17/11* (2006.01)
*A61B 5/00* (2006.01)
(Continued)

(52) U.S. Cl.
CPC ............ *A61B 17/11* (2013.01); *A61B 5/0066* (2013.01); *A61B 5/02007* (2013.01);
(Continued)

(58) Field of Classification Search
None
See application file for complete search history.

(56) References Cited

U.S. PATENT DOCUMENTS 5,694,206 A * 12/1997 Curtiss ............... G01N 21/8507
356/414
5,702,407 A * 12/1997 Kaji ................... A61B 17/0469
606/139

(Continued)

OTHER PUBLICATIONS

Huang et al., "Real-time 3D Fourier-domain optical coherence tomography guided microvascular anastomosis," Proc. SPIE 8671, Medical Imaging, Mar. 2013, 86711H-1-86711H-7.

(Continued)

*Primary Examiner* — Tse Chen
*Assistant Examiner* — Joanne Hoffman
(74) *Attorney, Agent, or Firm* — Venable LLP; Henry J. Daley (57) ABSTRACT

A surgical evaluation and guidance system for use in extravacular evaluation and guidance of fluid vessel surgeries, includes an optical coherence tomography engine; a vessel probe optically coupled to the optical coherence tomography engine; and a signal processing and display system adapted to communicate with the optical coherence tomography engine to receive imaging signals therefrom. An optical coherence tomography vessel probe for use in extravacular evaluation and guidance of fluid vessel surgeries, includes a probe body having a proximal end and a distal end; an optical relay system disposed within the probe body; and a vessel adapter at least one of attached to or integral with the probe body at the distal end of the probe body, wherein the vessel adapter defines a groove that is configured to accept one of a fluid vessel and a lymphaticovenous vessel.

22 Claims, 11 Drawing Sheets (51) Int. Cl.
*A61B 5/02* (2006.01)
*A61B 5/026* (2006.01)
*A61B 90/00* (2016.01)

(52) U.S. Cl.
CPC ............ *A61B 90/361* (2016.02); *A61B 90/37* (2016.02); *A61B 5/0261* (2013.01); *A61B 5/418* (2013.01); *A61B 2017/1107* (2013.01); *A61B 2090/3614* (2016.02); *A61B 2090/3735* (2016.02); *A61B 2505/05* (2013.01)

(56) References Cited

U.S. PATENT DOCUMENTS

| | | | | |
|---|---|---|---|---|
| 5,759,150 | A * | 6/1998 | Konou | A61B 17/00008 600/114 |
| 2002/0163622 | A1 * | 11/2002 | Magnin | A61B 5/0066 351/212 |
| 2002/0188204 | A1 * | 12/2002 | McNamara | A61B 1/00082 600/478 |
| 2003/0018262 | A1 * | 1/2003 | Manor | A61B 8/06 600/449 |
| 2003/0130654 | A1 * | 7/2003 | Kasahara | A61B 17/3421 606/45 |
| 2003/0231309 | A1 * | 12/2003 | Fulghum, Jr. | A61B 5/0071 356/338 |
| 2005/0143664 | A1 * | 6/2005 | Chen | A61B 5/6852 600/478 |
| 2007/0081166 | A1 * | 4/2007 | Brown | A61B 3/1005 356/479 |
| 2008/0306386 | A1 * | 12/2008 | Baba | A61B 8/06 600/455 |
| 2010/0185220 | A1 * | 7/2010 | Naghavi | A61B 5/14546 606/158 |
| 2011/0144661 | A1 * | 6/2011 | Houser | A61B 17/0057 606/142 |
| 2013/0301008 | A1 * | 11/2013 | Srivastava | G01B 9/02083 351/246 |
| 2014/0160462 | A1 | 6/2014 | Kang et al. | |
| 2014/0241596 | A1 * | 8/2014 | Chen | G06K 9/00885 382/124 |

OTHER PUBLICATIONS

Ibrahim et al., "3D Image Guided Micro-Vascular Anastomosis Using Ultra High Speed Fourier Domain Optical Coherence Tomography in Murine Vascularized Composite Allotransplantation Models," *AJT*, May 2012, (12):274-275.

Ibrahim et al., "3D Image Guided Reconstructive Microsurgery Using Ultra High Speed Fourier Domain Optical Coherence Tomography," 91st Annual Meeting of American Association of Plastic Surgeons, Apr. 14-17, 2012, 2 pages.

Kang et al., "Real-time three-dimensional Fourier-domain optical coherence tomography video image guided microsurgeries," J. Biomed. Opt. 17(8), 081403 (2012).

* cited by examiner

SYSTEMS, METHODS AND APPARATUSES FOR REAL-TIME ANASTOMOSIS GUIDANCE AND SURGICAL EVALUATION USING OPTICAL COHERENCE TOMOGRAPHY

GOVERNMENT INTEREST

This invention was made in part with Government Support under National Institutes of Health and National Institute of Neurological Disorders and Stroke grant no. 1R21NS063131-01A1, and under National Institutes of Health and National Eye Institute grant no. 1R01EY021540-01A1. The Government has certain rights in the invention.

TECHNICAL FIELD

The present invention relates to systems, methods and medical devices for use in guiding and evaluating vascular and lymphaticovenous anastomosis in real-time. More particularly, the invention relates to systems, methods and medical devices that use a surgical evaluation and guidance system for real-time guidance and evaluation.

BACKGROUND

Vascular and microvascular anastomosis is considered to be the foundation of plastic and reconstructive surgery, hand surgery, transplant surgery, vascular surgery and cardiac surgery. In the last two decades innovative techniques, such as vascular coupling devices, thermo-reversible poloxamers and suture-less cuff have been introduced. Intra-operative surgical guidance using a surgical imaging modality that provides in-depth view and 3D imaging can improve outcome following both conventional and innovative anastomosis techniques.

Optical coherence tomography (OCT) is a noninvasive high-resolution, high-speed, 3D imaging modality that has been adopted widely in biomedical and clinical applications. Since its invention in the early 1990s, OCT has been widely used for diagnosis, therapy monitoring and ranging. However, innovation in the field of surgical precision has failed to provide in-depth view and 3D guidance for microvascular surgery.

An important parameter to determine the surgical outcome is whether the blood flow has been restored. Because vessels are so delicate, endothelial injury, mal-positioned or partial thickness sutures can induce turbulence or thrombosis. If the thrombosis occludes the vessel lumen with no flow distally, all the previous steps have to be redone. However, sometimes the thrombus formation is not immediate or the thrombus is not large enough to completely occlude the vessel. In such a situation, visual input from an optical microscope can deceivingly show flow restoration.

Further, a suture technique described by Alexis Carrel and awarded the Nobel Prize in 1912 utilizes precise placement of sutures to connect two ends of vessels together. However, this technique has remained a challenge for surgeons to master, and thus requires the highest level of skill and surgical expertise, especially for small vessels smaller than 1 mm in diameter.

What is needed are systems, methods and apparatuses that can assist in inter-operative decision-making processes and to avoid post-operative complications while helping to improve surgical precision.

SUMMARY

In one embodiment, a surgical evaluation and guidance system for use in extravascular evaluation and guidance of fluid vessel surgeries, includes an optical coherence tomography engine; a vessel probe optically coupled to the optical coherence tomography engine; and a signal processing and display system adapted to communicate with the optical coherence tomography engine to receive imaging signals therefrom, wherein the vessel probe is configured to accommodate a fluid vessel in a position and orientation to provide a plurality of B-mode optical coherence tomography images displaced along the fluid vessel relative to each other, and wherein the signal processing and display system is configured to selectively display three-dimensional structural features of the fluid vessel and fluid flow through the fluid vessel. In another embodiment, an optical coherence tomography vessel probe for use in extravascular evaluation and guidance of fluid vessel surgeries, includes a probe body having a proximal end and a distal end; an optical relay system disposed within the probe body; and a vessel adapter at least one of attached to or integral with the probe body at the distal end of the probe body, wherein the vessel adapter defines a groove that is configured to accept one of a fluid vessel and a lymphaticovenous vessel.

Additional features, advantages, and embodiments of the invention are set forth or apparent from consideration of the following detailed description, drawings and claims. Moreover, it is to be understood that both the foregoing summary of the invention and the following detailed description are examples and intended to provide further explanation without limiting the scope of the invention as claimed.

DETAILED DESCRIPTION

Some embodiments of the current invention are discussed in detail below. In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated. All references cited in this specification are incorporated herein by reference.

The term "light" as used herein is intended to have a broad meaning that can include both visible and non-visible regions of the electromagnetic spectrum. For example, visible, near infrared, infrared and ultraviolet light are all considered as being within the broad definition of the term "light."

The term "real-time" is intended to mean that the OCT images can be provided to the user during use of the surgical evaluation and guidance system. In other words, any noticeable time delay between detection and image display to a user is sufficiently short for the particular application at hand. In some cases, the time delay can be so short as to be unnoticeable by a user.

Figure 1:
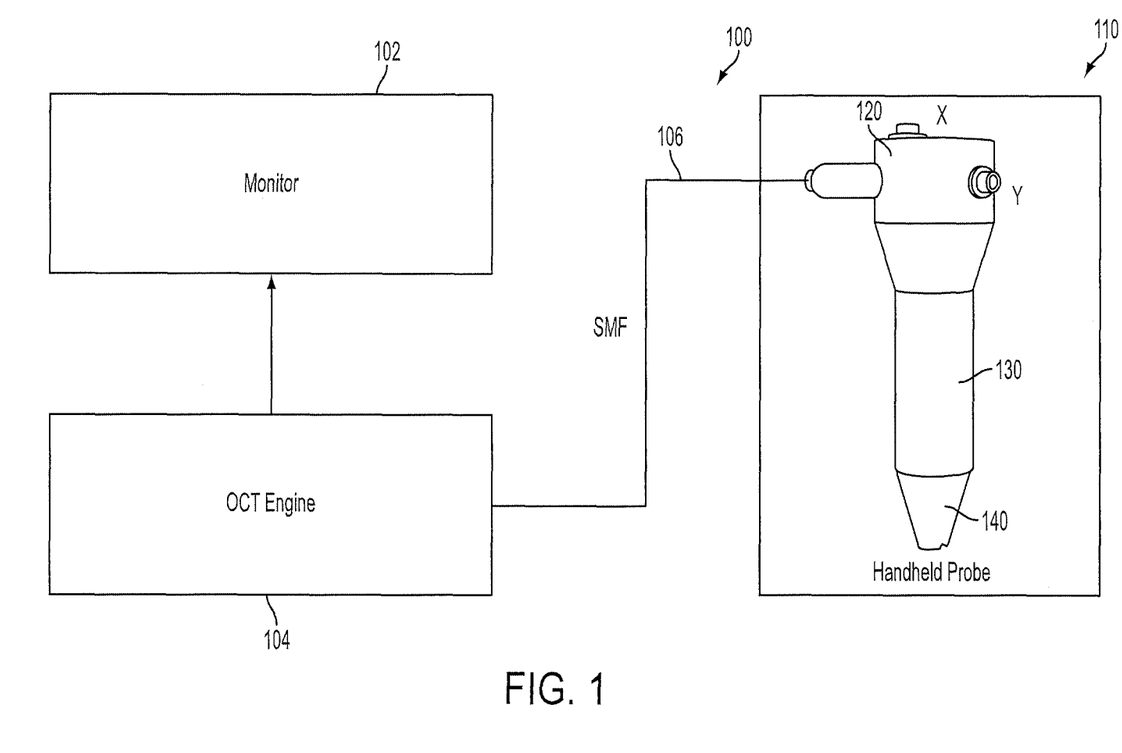
FIG. 1 shows an embodiment of a surgical evaluation and guidance system with guiding and evaluating capabilities.

In FIG. 1, a surgical evaluation and guidance system 100 for use in extravascular evaluation and guidance of fluid vessel surgeries includes an optical coherence tomography engine 104; a vessel probe 110 optically coupled to the optical coherence tomography engine 104; and a signal processing and display system 102 adapted to communicate with the optical coherence tomography engine 104 to receive imaging signals therefrom, wherein the vessel probe 110 is configured to accommodate a fluid vessel in a position and orientation to provide a plurality of B-mode optical coherence tomography images displaced along the fluid vessel relative to each other, and wherein the signal processing and display system 102 is configured to selectively display three-dimensional structural features of the fluid vessel and fluid flow through the fluid vessel.

A surgical evaluation and guidance system 100 according to some embodiments of the present invention can confirm and/or assess the surgical progress and result of a surgical site. After completion of a surgery, the surgical and evaluation system 100 can also help the surgeon evaluate and confirm the blood flow restoration, the quality of the blood flow, a property of the inner lumen tunnel connection, and early thrombosis formation.

In one embodiment of the present invention, a surgical evaluation and guidance system 100, as shown in FIG. 1, may include signal processing and display 102 that shows the real-time intraoperative images; the OCT engine 104; and the vessel probe 110 for convenient use. The vessel probe 110 may be optically coupled to the optical coherence tomography engine 104 via an optical fiber 106.

The signal processing and display 102 can be of the type disclosed in "3D Image Guided Reconstructive Microsurgery Using Ultra High Speed Fourier Domain Optical Coherence Tomography," Zuhaib Ibrahim, Qi Mao, Johanna Grahammer, Kate Buretta, Yong Huang, Joani Christensen, Nance Yuan, Jin U Kang, W P Andrew Lee, Gerald Brandacher, *AJT*, May 2012, (12):274-275, which is herein incorporated in its entirety by reference.

In some embodiments, real-time OCT and phase-resolved Doppler OCT (PRDOCT) can guide microvascular imaging, can guide microvascular anastomosis, can reduce the risk of technical failure and can provide immediate evaluation of surgical outcome. Furthermore, these imaging modalities can promptly diagnose early thrombus formation and predict its progression. The surgical guidance and evaluation system 100 can comprise Speckle Variance optical coherence tomography to image and access fluid flow. See U.S. application Ser. No. 13/709,874, the contents of which are herein incorporated by reference in its entirety. In OCT imaging speckle pattern forms due to the coherent superimposition of random phasors. As a result of speckle, an OCT signal becomes random in an area that is macroscopically uniform. If the sample under imaging is static, the speckle pattern is temporally stationary. However, when photons are backscattered by moving particles, such as cells in flowing blood, the formed speckle pattern changes rapidly over time. Thus speckle patterns at areas with flowing blood have a large temporal variation, which can be quantified by inter-frame speckle variance.

The OCT engine 104 can be a Fourier domain OCT system and can operate using either spatially-encoded frequency domain OCT (or spectral-domain OCT) or time-encoded frequency domain OCT (or swept-source OCT). The OCT engine 104 can be connected to an arbitrary single-mode fiber so that the OCT engine 104 can be arranged alongside a surgical table with proper position without causing too much congestion. The surgical guidance and evaluation system 100 can include Doppler optical coherence tomography.

Figure 2A:
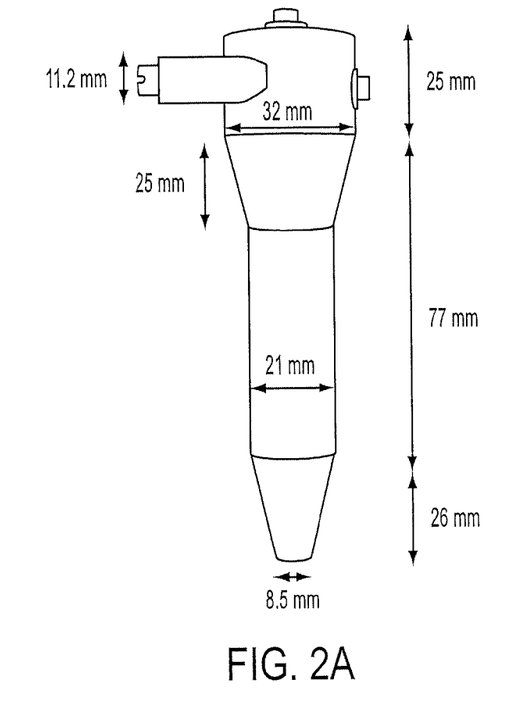
FIG. 2A shows dimensions of one embodiment of a vessel probe and FIG. 2B shows a CAD rendering of a cross section of the vessel probe.
Figure 2B:
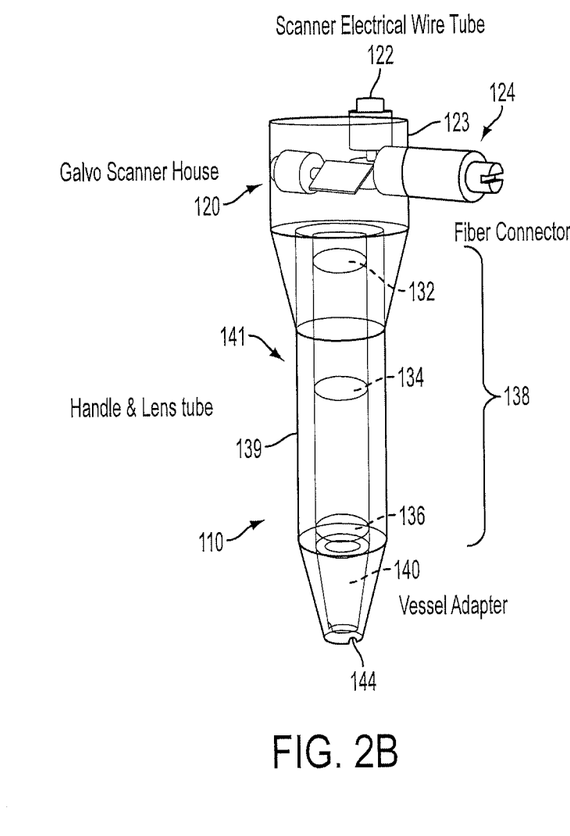

One embodiment of the vessel probe 110 will now be described, as shown in FIGS. 2A and 2B. In FIG. 2B, an optical coherence tomography (OCT) vessel probe 110 for use in extravascular evaluation and guidance of fluid vessel surgeries includes a probe body 130 having a proximal end and a distal end; an optical relay system 141 disposed within the probe body 140; and a vessel adapter 140 at least one of attached to or integral with the probe body 130 at the distal end of the probe body 130, wherein the vessel adapter 140 defines a groove 144 that is configured to accept one of a fluid vessel and a lymphaticovenous vessel.

The probe body 130 can serve as a lens housing. The probe body 130 can house an optical relay system 141. The probe body 130 can include an optical scanner 120, which can be a 2-D scanner. The optical scanner 120 can be disposed in the probe body 130 in an optical path between the optical port 123 and the optical relay system 141. The optical scanner can be a customized galvo scanner housing for either a two-dimensional scanning mirror pair or an MEMS mirror. The vessel probe 110 can include a vessel adapter 140 that may be attached to the probe body 130 at the distal end of the probe body 130. In another embodiment, the vessel adapter 140 may be integral with the probe body 130 at the distal end of the probe body 130. As shown in FIG. 2B, the vessel probe 110 can be formed such that the optical scanner 120 is adjacent to the probe body 130, which is adjacent to the vessel adapter 140. The optical scanner 120 can be substantially in the shape of a cylinder. The probe body 130 can be substantially in the shape of a cylinder. In another embodiment, at least a portion of the probe body 130 can have a frustoconical shape that narrows in diameter from a more proximal portion of the vessel probe 110 to a more distal portion of the vessel probe 110. The vessel adapter 140 can have a cylindrical shape. Another embodiment can have at least a portion of the vessel adapter 140 having a frustoconical shape.

The optical scanner 120 can include a scanner electrical wire tube 122 that houses electrical wires to be used to drive and control scanning mirrors. The optical scanner 120 can include an optical port 123 that is configured to be optically connected to the optical coherence tomography engine 104.

In one embodiment, the optical port 123 interfaces with an optical fiber connector 124 that is configured to house an arbitrary single-mode (or optical) fiber 106. The vessel probe 110 can be connected through the arbitrary single-mode fiber 106 to the OCT engine 104.

As shown in FIG. 2B, the probe body 130 can include an optical relay system 141 for performing beam focusing to a targeted sample surface. The optical relay system 141 can be a three-lens optical system 138. The first two lenses 132, 134 of the three-lens optical system 138 can form the optical relay system 141 that conveys a parallel beam coming out from the scanning mirrors to a parallel beam in front of the final focusing objective lens 136 without hitting probe body wall 139. The first and second lenses 132, 134 can have a focal length of about 30 mm while the third lens 136 can have a focal length of about 25 mm. The lenses 132, 134, 136 can have a diameter of about 12.7 mm.

FIG. 2A shows that the vessel probe 110 can have an overall length of about 137 mm and an average diameter of about 22 mm. However, the vessel probe 110 can have an overall length of at least 49 mm and up to 201 mm and can have an average diameter of at least 1 mm and up to 51 mm, for example, so that the vessel probe 110 is capable of being held in a hand. The optical scanner 120 can have a diameter of about 32 mm and a height of about 25 mm. The fiber connector 124 can be about 11.2 mm in diameter. The probe body 130 can have a height of 77 mm. As shown in FIG. 2A, the probe body 130 can have a frustoconical section that is 25 mm in height and a cylindrical portion of about 52 mm. The probe body 130 can have a diameter of about 32 mm at the widest portion of the frustoconical portion and can have a diameter of about 21 mm at the cylindrical portion. The vessel adapter 140 can have a height of about 26 mm. The vessel adapter 140 can have a diameter of about 21 mm at a top portion of the frustoconical portion and a diameter of 8.5 mm at the most narrow portion of the adapter 140.

Figure 3:
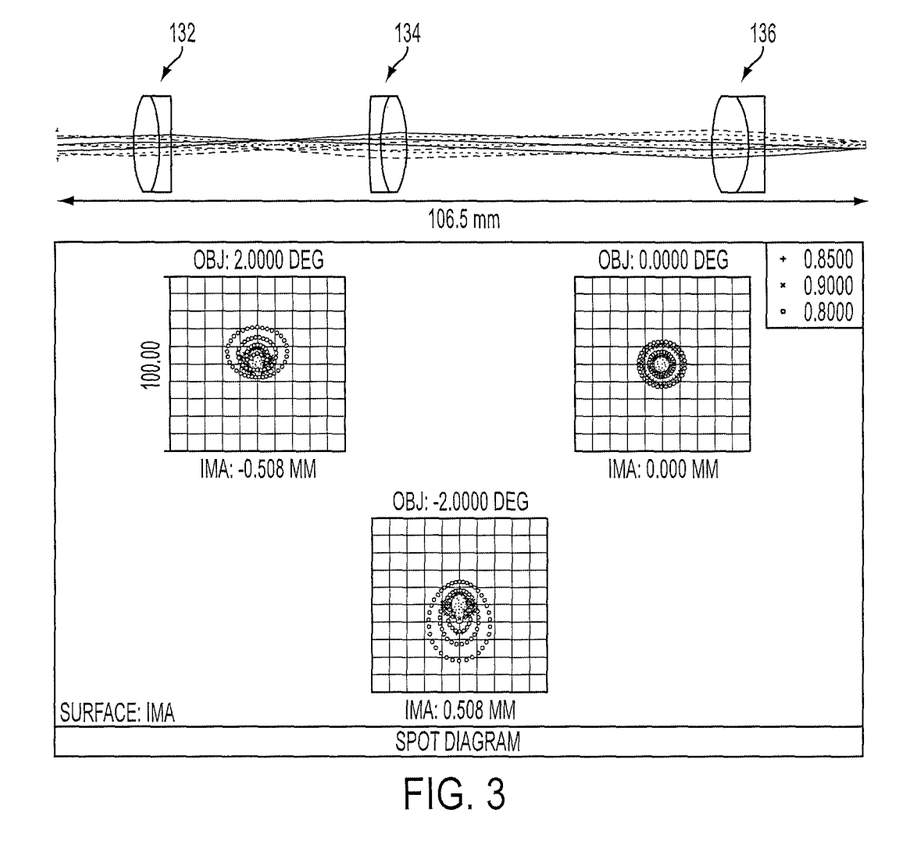
FIG. 3 shows a simulation result of an optical property of the surgical evaluation and guidance system.

As shown in FIG. 3, due at least in part to the three-lens optical system 138, a simulation result of the optical performance can be seen. In FIG. 3, the RMS beam spot radius is less than 10 micron for the whole imaging field considering three selective wavelengths in the whole source spectrum. The field of view can be designed to be between around 3 mm by 3 mm, which meets most of the anastomosis inspection requirements.

Figure 4A:
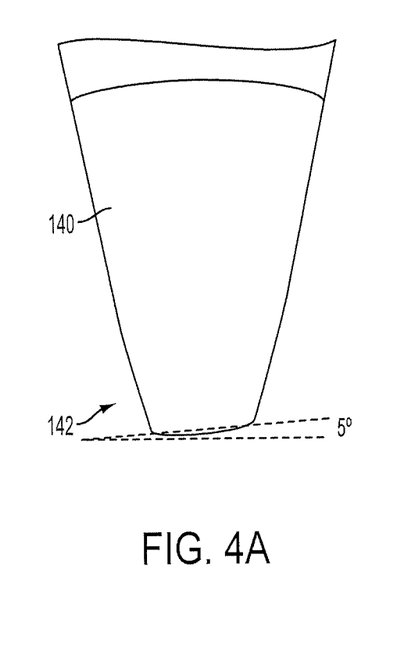
FIG. 4A shows a perspective illustrating an angle-cleaved tip of the vessel probe.
Figure 4B:
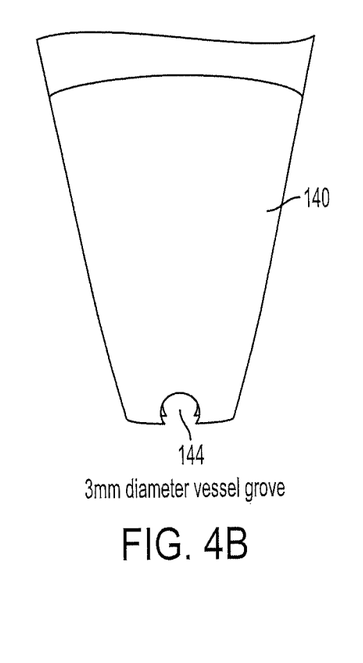
FIG. 4B shows a perspective which illustrates a groove at the tip.

In one embodiment, the vessel adapter 140 can be customized to accommodate a specific fluid vessel or lymphaticovenous vessel, as shown in FIGS. 4A and 4B. In FIG. 4A, a vessel groove 144 can be formed at the tip 142 of the vessel adapter 140, which can be at the far end of the vessel probe 110, to accommodate a fluid vessel or a lymphaticovenous vessel. The vessel adapter 140 may define the groove to facilitate positioning the fluid vessel. In FIG. 4B, the groove 144 can be formed along a line at an angle of about 5° to facilitate Doppler measurements. However, the groove of the vessel adapter 140 can be formed along a line at an angle between at least 4° and up to 21°. Thus, the top of the vessel adapter may be angle cleaved at a Doppler angle for Doppler OCT imaging. Different vessel sizes may have different groove diameters so that the vessel probe 110 is better adapted to each vessel. The vessel that sits in the groove 144 of the vessel adapter 140 can be assumed to be in a straight line. Thus, by combining the fixed Doppler angle, absolute blood flow can be calculated from the Doppler imaging, which can be of great clinical importance to surgeons.

Figure 5:
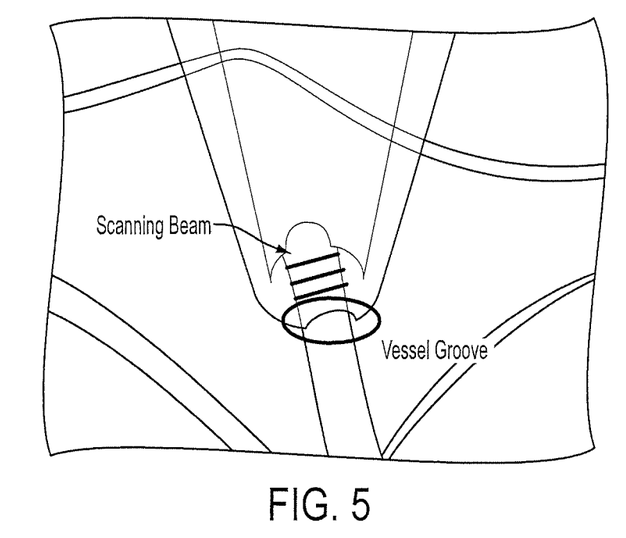
FIG. 5 shows the vessel probe adapted for vessel imaging.

One embodiment shown in FIG. 5 depicts the vessel probe 110 being used under actual surgical guidance and evaluation.

Figures 6A, 6B, 6C:
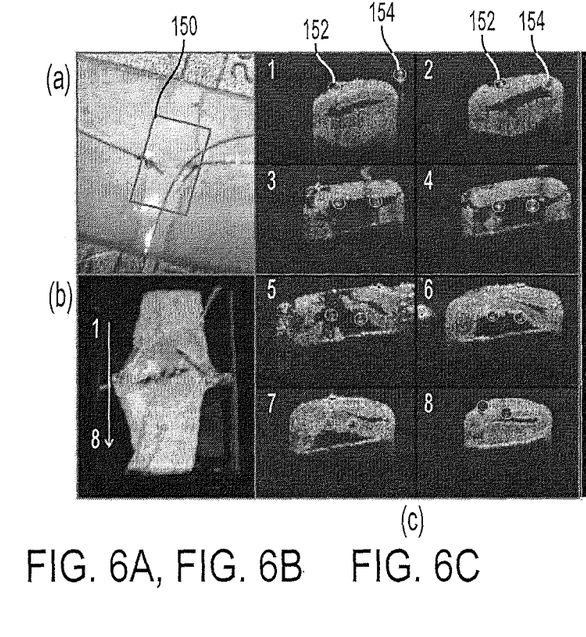
FIG. 6A shows the surgical microscope view of a transparent vessel of incorrect suture placement with two sutures tied and one suture going through both ends.
FIG. 6B is the corresponding top view volume rendering of the surgical site.
FIG. 6C consists of eight cross-sectional B-mode frames marked in the direction of the white arrow in FIG. 6B. Sutures were marked with yellow circles in FIG. 6C.

FIG. 6A shows a surgical microscopic view of a transparent vessel with two sutures tied and one suture going through both ends. For example, FIG. 6A shows a view of a red rectangular area 150 being imaged using OCT after putting a fourth suture through both vessel ends. FIG. 6B corresponds to a top view volume rendering of the surgical site. As can be seen from the Figure, a surgeon is offered a general scene of the surgical site based on the images. For example, first and second ties are at the vessel edge and third and fourth ties proceed through both vessel ends. FIG. 6C shows eight cross-sectional B-mode frames marked in the direction of the white arrow in FIG. 6B. In FIG. 6C, third and fourth sutures are marked with yellow circles 152, 154, respectively.

Figure 6D:
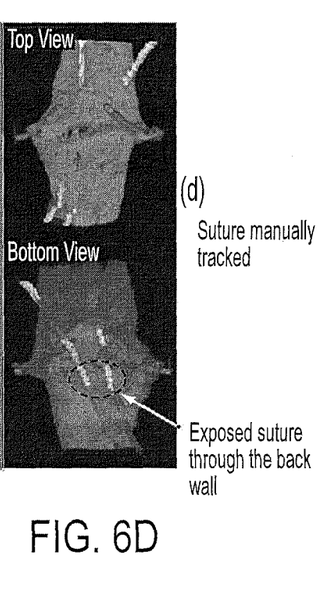
FIG. 6D shows volumetric rendering from top and bottom views of the anastomosed site with sutures manually segmented out.
Figure 7:
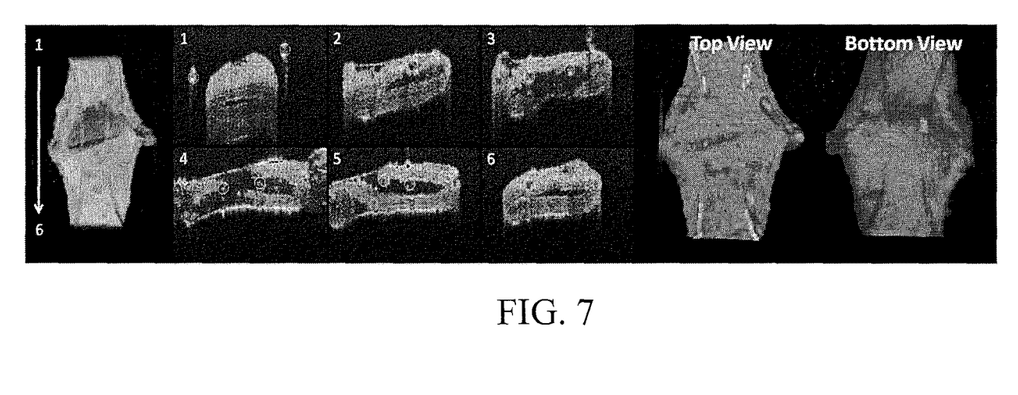
FIG. 7 shows visualization of the vessel probe of accurate suture placement relative to the vessel walls.

FIG. 6D shows a volumetric rendering from top and bottom views of the anastomosed site with sutures manually segmented out. Thus, in one embodiment, segmentation can be performed manually to determine the vessel structure and suture locations. Segmentation software can benefit the accuracy of error detection and results prediction. However, segmentation software is not necessary. With this suture placement, error can easily be recognized as the suture is exposed over both vessels at one end. Thus, FIG. 6D illustrates an example of technical error where an accidental back wall suture occludes the vessel lumen. As noted above, these B-mode frames of FIG. 6C represent eight slices over the imaging volume to trace the sutures through both vessel walls. As can be seen from the two yellow circles 152, 154 marked out in FIG. 6C, the third and fourth sutures accidentally protrude through both anterior and posterior walls of the bottom vessel, and hence occlude the lumen. In this regard, the suture lies within the adventitia of the posterior wall and could not be visualized through the optical microscope. Having detected this error by the OCT image through use of the vessel probe, the surgeon can re-do the third and fourth sutures to successfully perform the anastomosis.

In contrast to FIGS. 6A-6D, FIG. 7 represents a successful and accurate suture placement relative to the vessel walls. In this case, having detected no errors by the OCT imaging through use of the vessel probe, the surgeon could continue to perform the rest of the sutures.

Figure 8:
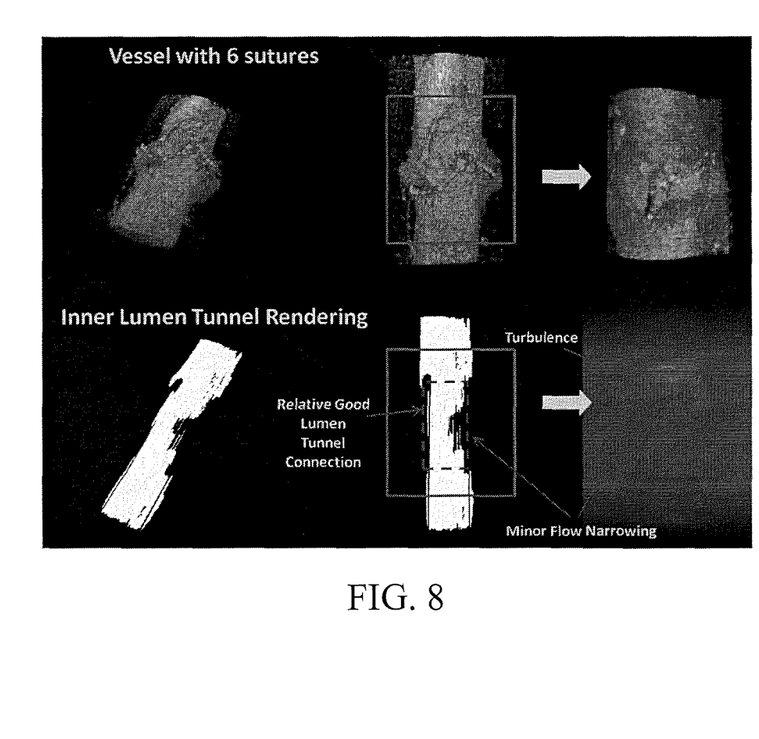
FIG. 8 shows relative good inner lumen connection inspected through the vessel probe and poster surgical volumetric Doppler blood flow rendering.
Figure 9:
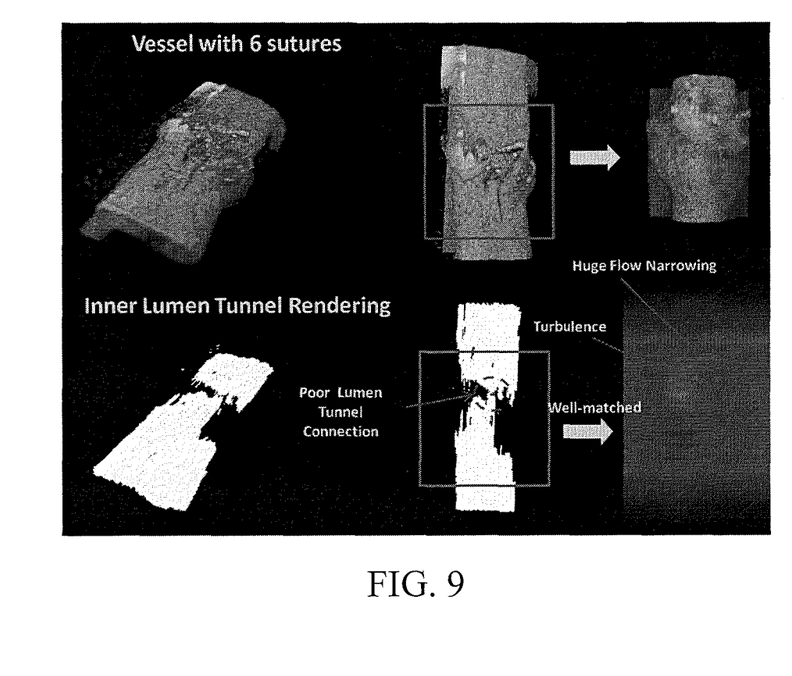
FIG. 9 shows poor lumen connection inspected through OCT and poster surgical volumetric Doppler blood flow rendering.

FIG. 8 shows a mouse femoral artery anastomosis experiment with relatively good vessel lumen connection. On the other hand; FIG. 9 shows one femoral artery anastomosis experiment with poor vessel lumen connection. In each of these Figures, inner lumen areas are manually segmented out. Vessel narrowing and flow turbulence can be easily visualized through the Doppler images. In Doppler imaging, a blue color indicates a flow towards the scanning beam while a red color indicates a flow away from the scanning beam.

Figure 10:
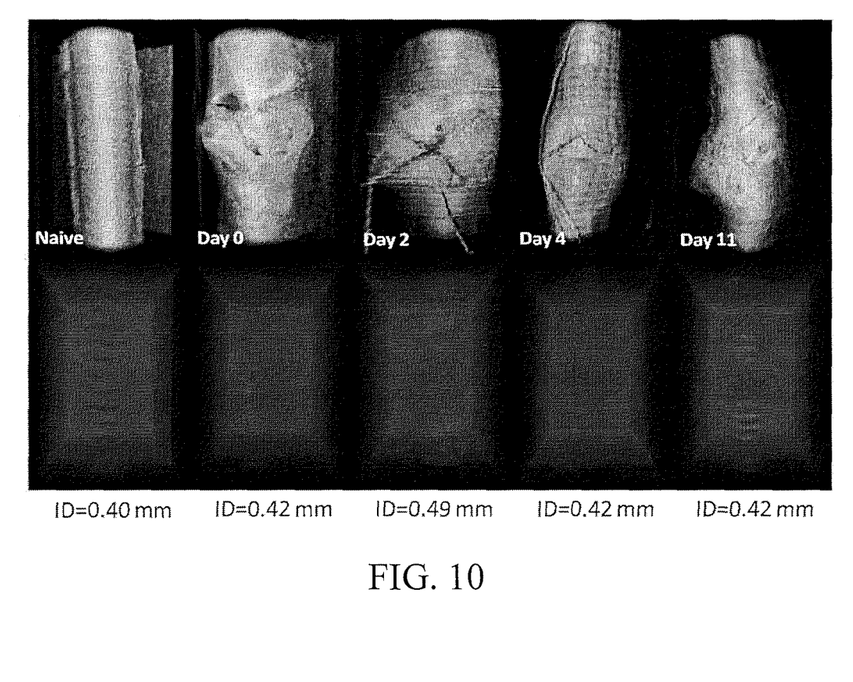
FIG. 10 shows a long-term study of a rat femoral artery anastomosis.

FIG. 10 shows a long term study of a rat femoral artery anastomosis over 11 days. The Figure shows naïve healthy flow state and the graduation blood flow restoration over time. At the same time, structural information using volumetric data can be extracted and thrombosis can be visualized through the cross-sectional images.

Figure 11:
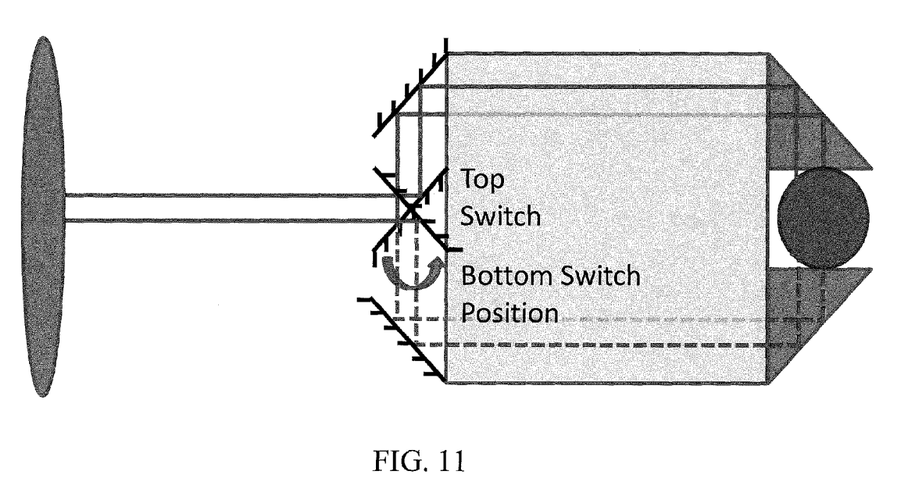
FIG. 11 shows a vessel probe being used to image both sides of a vessel wall.

While in one embodiment the vessel probe can be used to image one side of a vessel wall, in another embodiment shown in FIG. 11, the vessel probe can be used to image both sides of the vessel wall to study the circumferential property of the whole vessel. In such a configuration, a switchable mirror is used to position the mirror to either a top or bottom-switch position to direct a beam of light along a top passage or to a bottom passage. Such a configuration allows the imaging of the whole vessel even when blood flow is restored into the vessel. A top and a bottom volume image can later be registered to form the whole vessel structure using customized software.

Further, certain clinical parameters can be extracted from the volumetric imaging and certain software can be developed into the current system. Although preliminary results are based on the sutured anastomosis, the vessel probe of one embodiment can also be used for other non-sutured anastomosis to improve and evaluate the surgical outcome.

While in one embodiment, systems, methods and apparatuses can be directed to vessel anastomosis, it can be additionally feasible to direct the systems, methods and apparatuses to work under lymphaticovenous anastomosis.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. A surgical evaluation and guidance system for use in extravascular evaluation and guidance of fluid vessel surgeries, comprising:
   an optical coherence tomography engine;
   a vessel probe optically coupled to the optical coherence tomography engine, the vessel probe having a longitudinal axis; and
   a signal processing and display system adapted to communicate with the optical coherence tomography engine and receive imaging signals therefrom,
   wherein the vessel probe is configured to accommodate a fluid vessel in a position and orientation to provide a plurality of B-mode optical coherence tomography images displaced along the fluid vessel relative to each other,
   wherein the signal processing and display system is configured to selectively display three-dimensional structural features of the fluid vessel and fluid flow through the fluid vessel, and
   wherein the vessel probe comprises a vessel adapter attached to a distal end thereof, the vessel adapter defining a vessel groove to facilitate positioning the fluid vessel, and a distal end of the vessel adapter having an inclined surface with respect to the longitudinal axis to facilitate measurements of the optical coherence tomography images of the fluid vessel, the inclined surface being in a range of 4-21 degrees with respect to the longitudinal axis of the vessel probe.

2. The surgical evaluation and guidance system according to claim 1, wherein the vessel probe is configured to accommodate at least one of blood vessels and lymphatic vessels.

3. A surgical evaluation and guidance system according to claim 1, wherein the surgical evaluation and guidance system comprises Doppler optical coherence tomography, and
   wherein the inclined surface is configured to facilitate acquisition of Doppler optical coherence tomography signals.

4. A surgical evaluation and guidance system according to claim 1, wherein the signal processing and display system is configured to selectively display three-dimensional structural features of said fluid vessel and fluid flow through the fluid vessel in real time during a procedure for evaluating or repairing the fluid vessel.

5. A surgical evaluation and guidance system according to claim 1, wherein said vessel probe has a size and shape to be hand operable during surgical guidance and evaluation.

6. An optical coherence tomography (OCT) vessel probe for use in extravascular evaluation and guidance of fluid vessel surgeries, comprising:
   a probe body having a proximal end and a distal end, wherein the probe body defines an optical port, the probe body having a longitudinal axis;
   an optical relay system disposed within said probe body; and
   a vessel adapter at least one of attached to or integral with said probe body at said distal end of said probe body, wherein said vessel adapter defines a vessel groove that is configured to accept one of a fluid vessel and a lymphaticovenous vessel to facilitate positioning the fluid vessel, and a distal end of the vessel adapter having an inclined surface with respect to the longitudinal axis to facilitate measurements of the optical coherence tomography images of the fluid vessel, the inclined surface being in a range of 4-21 degrees with respect to the longitudinal axis of the vessel probe; and
   an optical scanner disposed in said probe body in an optical path between said optical port and said optical relay system, wherein said optical scanner is configured to generate said data of said three-dimensional structural features and fluid flow of the fluid vessel or lymphaticovenous vessel.

7. The OCT vessel probe according to claim 6, wherein the optical port is configured to be optically connected to an optical coherence tomography engine.

8. The OCT vessel probe according to claim 7, further comprising an optical fiber connector attached to said probe body, said optical fiber connector being structured to attach to an optical fiber of said optical coherence tomography engine.

9. The OCT vessel probe according to claim 6, wherein the optical scanner comprises a galvo actuated two-dimensional scanning mirror pair.

10. The OCT vessel probe according to claim 6, wherein the optical scanner comprises a micro-electromechanical system mirror.

11. The OCT vessel probe according to claim 6, wherein the relay optical system comprises a plurality of lens elements.

12. The OCT vessel probe according to claim 11, further comprising an objective optical system for performing beam focusing on a targeted sample surface.

13. The OCT vessel probe according to claim 6, wherein said groove of said vessel adapter extends along a plane that has an angle of about 5°-20° with respect to an upper diameter cross-section of the probe, the angle of the vessel adapter plane being configured to facilitate Doppler measurements.

14. The OCT vessel probe according to claim 13, wherein the angle is about 5°.

15. The OCT vessel probe according to claim 6, wherein a height of the OCT vessel probe is at least 49 mm and up to 200 mm.

16. The OCT vessel probe according to claim 15, wherein the height is 137 mm.

17. The OCT vessel probe according to claim 6, wherein the probe body has an average diameter of at least 1 mm and up to 50 mm.

18. The OCT vessel probe according to claim 17, wherein the average diameter is 22 mm.

19. The OCT vessel probe according to claim 6, wherein the vessel adapter has a frustoconical shape, wherein a diameter of the vessel adapter is narrower at the tip of the vessel adapter.

20. A surgical evaluation and guidance system according to claim 3, wherein the groove is formed to run along a longitudinal axis of the vessel at an angle of the inclined surface with respect to an upper diameter cross-section of the probe.

21. A surgical evaluation and guidance system according to claim 20, wherein the angled surface is in a range of 5-20 degrees.

22. A surgical evaluation and guidance system according to claim 21, wherein the angled surface is 5 degrees.

* * * * *

UNITED STATES PATENT AND TRADEMARK OFFICE
CERTIFICATE OF CORRECTION

PATENT NO. : 9,782,175 B2
APPLICATION NO. : 14/261275
DATED : October 10, 2017
INVENTOR(S) : Jin U. Kang et al.

Page 1 of 1

It is certified that error appears in the above-identified patent and that said Letters Patent is hereby corrected as shown below:

In the Specification

Please replace Column 1, Lines 8-13 with the following:
This invention was made with government support under 1R21NS063131-01A1 and 1R01EY021540-01A1, awarded by the National Institutes of Health. The government has certain rights in the invention.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*